United States Patent [19]

Ayen et al.

[11] Patent Number: 4,681,959

[45] Date of Patent: Jul. 21, 1987

[54] PREPARATION OF INSOLUBLE METAL ALKOXIDES

[75] Inventors: Richard J. Ayen, Darien, Conn.; Johst H. Burk, Mohegan Lake; Carl C. Greco, Garnerville, both of N.Y.

[73] Assignee: Stauffer Chemical Company, Westport, Conn.

[21] Appl. No.: 725,847

[22] Filed: Apr. 22, 1985

[51] Int. Cl.$^4$ .............. C07F 7/28; C07F 7/00; C07F 1/00; C07F 3/00; C07F 5/00; C07F 5/02

[52] U.S. Cl. .............. 556/54; 556/56; 556/1; 568/841; 568/851; 558/296

[58] Field of Search .............. 556/54, 56, 1; 260/462 R; 568/841, 851; 558/296

[56] References Cited

U.S. PATENT DOCUMENTS

| | | |
|---|---|---|
| 2,114,866 | 4/1938 | Vaughn . |
| 2,187,821 | 1/1940 | Nellen . |
| 2,615,032 | 10/1952 | Harrington . |
| 2,621,194 | 12/1952 | Balthis . |
| 2,654,770 | 10/1953 | Herman . |
| 2,655,523 | 10/1953 | Herman . |
| 2,663,720 | 12/1953 | Hill . |
| 2,684,972 | 7/1954 | Haslam . |
| 2,773,083 | 12/1956 | Schmidt et al. . |
| 2,977,378 | 3/1961 | Kasper . |
| 3,061,623 | 10/1962 | Mador et al. . |
| 3,091,625 | 5/1963 | Gilsdorf . |
| 3,119,852 | 1/1964 | Gilsdorf . |
| 3,268,566 | 8/1966 | Stanley et al. . |
| 3,306,918 | 2/1967 | Schenck et al. . |
| 3,547,966 | 12/1970 | Marble . |
| 3,641,079 | 2/1972 | Termin et al. . |
| 3,721,689 | 3/1973 | Bardinet . |
| 3,752,834 | 8/1973 | Bardinet et al. . |
| 3,754,011 | 8/1973 | Hoch . |

OTHER PUBLICATIONS

Bischoff et al., J.A.C.S. 46, 256 (1924).
Bradley et al., Metal Alkoxides, Academic Press, London, Chapter 2, pp. 10 to 27 (1978).

Primary Examiner—Helen M. S. Sneed

[57] ABSTRACT

A number of processes for the formation of insoluble metal alkoxides are disclosed. In one embodiment, there is disclosed a two step process wherein a halide of an at least divalent metal is reacted with an appropriate alcohol in the first step. In the second step, the intermediate compound formed is then reacted with more alcohol, said alcohol forming part of a solvent system in which the final metal alkoxide formed is insoluble. In another embodiment, a two step process is disclosed wherein the intermediate formed in the first step is isolated, and then in the second step the intermediate is reacted with an appropriate alcohol to yield the final product. The final embodiment of the present invention comprises a one step process for the production of insoluble metal alkoxides wherein a halide of an at least divalent metal is reacted with an appropriate alcohol in the presence of an excess amount of a hydrogen halide acceptor in a solvent in which the hydrogen halide compound formed is soluble.

17 Claims, No Drawings

PREPARATION OF INSOLUBLE METAL ALKOXIDES

FIELD OF THE INVENTION

The present invention relates to improved processes for the production of insoluble metal alkoxides.

BACKGROUND OF THE INVENTION

Metal alkoxides are used for a wide variety of purposes. They are commonly employed catalysts in Ziegler polymerizations as well as in transesterification and condensation reactions. With partial or complete hydrolysis, alcoholysis or transesterification, they are used in coatings for plastics, textiles, glass and metals. Metal alkoxides are also used as additives for adhesives and paints and for the cross-linking or hardening of natural and synthetic materials.

Metal methoxides are also used for a wide variety of purposes. For example, tetramethyl titanate is used as a catalyst in the esterification of carboxylic acids with monohydric or polyhydric alkanols, particularly in the preparation of unsaturated esters which tend to polymerize in the presence of other esterification catalysts, thus reducing the yield of the monomeric ester. Tetramethyl titanate is also used as an ester interchange catalyst in the manufacture of higher esters from lower esters and as a catalyst in the manufacture of polyesters. Other metal methoxides can be used for similar purposes.

A commonly employed procedure for the production of metal alkoxides involves the reaction of a metal halide with an alcohol with the consequent generation of hydrogen halide. In order to progress to total alkoxylation of the metal, it is necessary that a hydrogen halide acceptor be present. Various patents disclosing the above reaction or variations on the above reaction are known.

The Nelles process, disclosed in U.S. Pat. No. 2,187,821, reacts a titanium tetrahalide with an alcohol in the presence of ammonia or an aliphatic or aromatic amine as a hydrogen halide acceptor. The reaction is also carried out in the presence of an inert organic solvent since the hydrogen halides formed are insoluble and easily separated.

A process for the conversion of titanium tetrahalides to titanate esters using amines and sulfonamides as catalysts is disclosed in U.S. Pat. No. 3,641,079. The reaction can be carried out in the liquid phase by using inert solvents.

U.S. Pat. No. 3,752,834 discloses the preparation of alkyl titanates by esterifying titanium tetrachloride with an alkanol, neutralizing the hydrochloric acid with ammonia and keeping the pH of the reaction mixture at about 4-6 until all the titanium tetrachloride has been introduced. Ammonia is then introduced until the pH of the reaction mixture is about 9.

U.S. Pat. No. 2,684,972 discloses a process for the production of inorganic esters wherein a metal halide is first reacted with ammonia and then the ammoniated compound is reacted with the appropriate alcohol. In the first step of the process disclosed in the above patent, the amount of ammonia added should be such that four atoms of nitrogen are combined with each titanium atom.

U.S. Pat. No. 2,654,770 discloses a method for the production of alkyl titanates wherein ammonia, a metal halide and an alcohol are admixed together to form an alkyl titanate and ammonium chloride. The ammonium chloride formed is then contained in a nitrogenous liquid selected from the group consisting of amides and nitriles.

U.S. Pat. No. 2,655,523 discloses a process for the formation of alkyl titanates wherein the ammonia used as the hydrogen chloride acceptor is present in slightly excess amounts.

U.S. Pat. No. 2,114,886 discloses a process for the purification of alkyl silicates wherein an alkyl silicate is treated with an amine to remove any residual hydrogen halide. The nitrogenous compound employed is soluble in the inorganic ester to be purified.

U.S. Pat. No. 3,268,566 discloses a process for the production of tetramethyl titanate wherein a tetraalkyl titanate is reacted with an alkanol.

U.S. Pat. No. 3,119,852 discloses a process for the formation of alkyl titanates wherein the alcohol is added to the titanium tetrachloride in a reverse addition mode. This patent also discloses the use of a solvent in which the ammonium chloride is insoluble.

U.S. Pat. No. 3,547,966 discloses a process for the production of trialkoxy monohalide titanium compounds. The reaction proceeds to the monohalide level (trialkoxy compound) when it is conducted at higher temperatures using a solvent whose boiling point is about the temperature at which the reaction is run.

French Patent of Addition, No. 92,060 reported at CA 71 91631, discloses the preparation of halogenated phenoxysilanes by reacting pentachlorophenol and trichlorosilane in the present of N,N'dimethylaniline.

While the processes detailed in the above patents are suited for the production of metal alkoxides derived from higher alcohols, i.e. $C_2$–$C_{20}$ alkanols, they are not suitable for the production of metal alkoxides derived from lower alcohols, particularly methanol. These methoxides are often solids and it is difficult to separate them from the solid ammonium chloride formed. Separation problems also occur since ammonium chloride and solid metal methoxides exhibit similar solubility characteristics toward most commonly employed organic solvents. The alternative process for the production of a methoxide, such as tetramethyl titanate, involves either a transesterification or a trans alcoholysis exchange. While somewhat feasible alternatives, such processes are also expensive.

SUMMARY OF THE INVENTION

In accordance with the present invention, there are disclosed a number of improved processes for the production of metal alkoxides.

In one embodiment of the present invention, a two step process for the production of metal alkoxides insoluble in the organic solvent used is disclosed. In this embodiment, a halide of an at least divalent metal is reacted with an appropriate alcohol under reaction conditions in which the hydrogen halide generated can be driven off. The intermediate produced in the above reaction, a halo alkoxy metal compound, is then reacted with more alcohol using an amine as a hydrogen halide acceptor. The second reaction is carried out in a solvent system in which the amine hydrochloride formed is soluble. Since the metal alkoxide formed is insoluble in the particular solvent system used, it precipitates out of solution and can be easily recovered.

In another embodiment of the present invention, the first step of the above process is run using an aromatic organic solvent in which the hydrogen halide formed is insoluble. The halo alkoxy metal compound formed is isolated and the solvent stripped. The halo alkoxy metal compound stripped of solvent can then be dissolved in the alkanol from which the alkoxy group is derived and the reaction can proceed to the final alkoxide stage using an amine as a hydrogen halide acceptor, said amine forming an amine hydrohalide soluble in the alkanol used. The above process thus obviates the need for an aromatic organic solvent in the second step.

In yet another embodiment of the present invention, a one-step process for the production of insoluble metal alkoxides is disclosed. The one-step process for the production of the insoluble metal alkoxide comprises the addition of an excess of amine over the amount of halide atoms on the metal halide used. In this embodiment, an excess of the alcohol is also used and the reaction is carried out in an alcohol in which the amine hydrohalide formed is soluble and the metal alkoxide formed is insoluble.

Further embodiments of the present invention may be seen in the Detailed Description of the Invention which follows.

DETAILED DESCRIPTION OF THE INVENTION

The present invention is directed to improved processes for the production of metal alkoxides which are insoluble in organic solvents. The present processes are especially suited for the isolation of a metal alkoxide produced as the result of an esterification reaction between a metal halide and an appropriate alcohol. While any halide of an at least divalent metal may be used, the preferred reaction is between a tetravalent metal halide and an alcohol.

In one embodiment of the present invention, a two step process for the production of metal alkoxides is disclosed. This process will be discussed in connection with the reaction between a tetravalent halide and an alcohol, although it is to be understood that the discussion applies equally to the reaction between any halide of an at least divalent metal and the appropriate alcohol.

In the first step of the above process, displacement of at least one of the halide atoms by an alkoxy group takes place readily to produce a haloalkoxy metal compound in a reaction which may be expressed as follows:

$$MX_n + mROH \xrightarrow{N_2} M(OR)_mX_{n-m} + mHX \quad (I)$$

wherein M is an at least divalent metal, X is a halogen, R is alkyl, n is an integer from 2–4 and m is an integer from 1–2. In this particular embodiment, it is preferred to drive off the hydrogen halide produced with an inert gas such as nitrogen and recover the hydrogen halide to be recycled or used for commercial purposes. Removal of the hydrogen halide also reduces the formation of alkyl chloride and insures that the reaction will proceed in the direction of the formation of the halo alkoxy compounds.

In order to produce further substituted compounds, the intermediate produced as a result of step (I) is then reacted with additional alcohol. In this step, the presence of a hydrogen halide acceptor is necessary for progression to the final alkyl, for example, tetraalkyl, compound of the metal. The second step of the process may be expressed as follows:

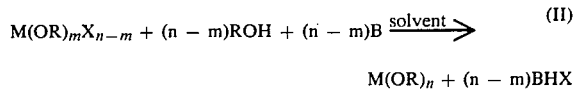

$$M(OR)_mX_{n-m} + (n-m)ROH + (n-m)B \xrightarrow{solvent} \quad (II)$$
$$M(OR)_n + (n-m)BHX$$

wherein M, R, n and m are as previously defined and B is a hydrogen halide acceptor.

In this embodiment of the present invention, it has now surprisingly been found that the solvent and the hydrogen halide acceptor used in reaction II can be chosen so as to produce a metal alkoxide in high yields. This surprising effect is achieved since the hydrogen halide acceptor used forms a hydrogen halide compound soluble in the solvent system used. Since the preferred alkoxide formed is insoluble in the solvent, it precipitates from the solution and can be recovered without the necessity of removing the hydrogen halide compound since the hydrogen halide remains dissolved in the solvent.

In the above embodiment, it has proven extremely useful to use a solvent system comprising an organic aromatic solvent/alcohol and the like. The choice of the organic aromatic solvent employed is, of course, determined by the solubility of the hydrogen halide compound in said solvent. Suitable solvent systems include toluene/methanol, xylene/methanol and the like. As used hereinafter, the term "organic aromatic" solvent includes toluene, xylene and the like and does not encompass alkanols. The ratio of the organic solvent used to the final product desired is determined by the particular hydrogen halide acceptor used. A particularly useful alcohol is methanol.

In another embodiment of the present invention, the two-step process can be modified so as to allow the isolation of the halo alkoxy metal compound produced in the first step. This modification also allows the second step of the process to be carried out without the necessity for an additional organic aromatic solvent. In this embodiment of the invention, the first step is run in an organic aromatic solvent in which the hydrogen halide formed is insoluble. Thus, the hydrogen halide formed is removed from the solution almost as fast as it is formed. Passage of an inert gas through the system will remove the formed hydrogen halide even faster. The first solvent is then stripped and the halo alkoxy metal compound can then be dissolved in an alcohol. The second step of the process is then carried out in the presence of a hydrogen halide acceptor and the hydrogen halide compound formed is soluble in the alcohol, thus the metal alkoxide formed easily precipitates from the solution since it is insoluble in the alcohol. If desired, the halo alkoxy compound isolated in the first step can also be used to form mixed alkoxides wherein the remaining halo groups or the halo alkoxy compound can be replaced by alkoxy groups different from the alkoxy group of the intermediate. Suitable solvents for this reaction include toluene, xylene and the like. A particularly suitable alcohol is methanol.

Yet another embodiment of the present invention comprises a one-step process for the production of insoluble metal alkoxides. In this one-step process, a halide of an at least divalent metal is reacted with the appropriate alcohol in the presence of an excess of the hydrogen halide acceptor. This reaction can be run in alcohol without the necessity of additional organic aromatic solvents. If a tetravalent metal halide is used, an amount ranging from about at least 4 to about 5 moles of the hydrogen halide acceptor per mole of the tetravalent metal halide can be used.

In all embodiments of the present invention, preferred hydrogen halide acceptors which can be used include amines such as triethylamine, tributylamine, tripropylamine and trioctylamine as well as higher molecular weight amines such as ALAMINE ® 336 amine (Henkel), a tertiary $C_8$–$C_{16}$ amine. The preferred amines are tertiary amines. The major consideration governing the choice of amine is that the amine hydrohalide must be soluble in the solvent or solvent system employed. It is also apparent that combinations of the above amines may also be used.

Examples of metal halides which may be used in the processes of the present invention include halides of group II-A metals such as strontium or barium, halides of group III-A and III-B metals such as gallium, indium, boron and yttrium and halides of group IV-A metals such as titanium, zirconium and hafnium. The metal halide used is chosen based on the fact that the final metal alkoxide formed must be one that is insoluble in the organic solvent. For a reason not readily explained, if halides or non-tetravalent metals, i.e. those appearing in groups II and III of the periodic table, are used, only those elements appearing in the latter part of the periodic table, i.e. periods 5–7, form metal alkoxides insoluble in organic solvents.

Suitable halides include the chlorides of the above metals. The preferred chlorides are the tetrachlorides although the dichlorides and trichlorides can also be used. While somewhat more expensive, the bromides, iodides and fluorides, in the di-, tri, and tetrasubstituted form, can also be used.

The alcohol from which the alkoxy group is derived is preferably methanol. The methoxides formed as a result of the reaction between a metal halide and methanol are generally insoluble in organic solvents. Higher alcohols may also be used provided that the metal alkoxide formed is insoluble in organic solvents.

The compounds produced by the processes of the present invention can be the dialkoxy, trialkoxy or tetraalkoxy metal compound. The present invention is particularly suited for the production of tetraalkoxy metal compounds with one especially preferred compound being tetramethyl titanate, a compound whose utility has been previously discussed.

In those processes of the present invention wherein a two-step process is disclosed, the reactions of Step I take place readily, usually by combining suitable amounts of the metal halide and alcohol. The hydrogen halide generated can be driven off by passage of an inert gas through the reaction mixture. If desired, the hydrogen halide may be recovered and used for commercial purposes. Since the reaction of Step I involves the replacement of one half of the halide atoms by the alkoxy group of the alcohol, the metal halide and alcohol are combined in a 1:2 ratio, respectively.

In those processes which involve a two step reaction, step II of the process, that is, the reaction between the intermediate produced in step I and the alcohol, also takes place readily, usually by combining suitable amounts of the intermediate and alcohol. Since this step also involves the replacement of the remaining halide groups by the alkoxy group of the alcohol, the ratio of the intermediate to alcohol is sufficient to accomplish this result. In the case of a dialkoxy, dihalo intermediate, the intermediate and alcohol would be combined in a 1:2 ratio respectively.

In those processes using a two step reaction, the amine used as a hydrogen halide acceptor in the second step is used in an amount sufficient to combine with the hydrogen All reactions of the present invention can be carried out at room temperature and atmospheric pressure although it is preferred to carry out the reaction at the reflux temperature of the solvent.

The order of addition of the reactants is not critical. Preferably, the alcohol is added to the metal halide dissolved in the solvent.

In all reactions the hydrogen halide formed can be regenerated using conventional techniques. For instance, if an amine hydrochloride is formed, it can be regenerated by using caustics, such as sodium or potassium hydroxide.

The present invention is illustrated by the following examples:

EXAMPLE 1

This example illustrates the reaction of titanium tetrachloride with methanol using tributylamine as a hydrogen chloride acceptor.

To a 500 milliliter 3-necked round bottomed flask fitted with a glass stirrer, condenser, dropping funnel and adapter with a gas inlet tube for the introduction of nitrogen were added 120 cc of toluene and 35 grams (0.184 mole) of titanium tetrachloride. To the dropping funnel was added 15 grams (0.48 mole) of methanol and the methanol was added dropwise over a 15 minute period to the titanium tetrachloride. During the methanol addition step, nitrogen was passed through the solution at the rate of 500 cc/min. After all the methanol had been added, the reaction mixture was refluxed for two hours, then cooled to 50° C. The nitrogen flow was then stopped and 70 cc of methanol was added. With vigorous stirring, 73 grams of tributylamine was added over a 30 minute period. During the amine addition, tetramethyl titanate began to precipitate out. After the amine had been added, the reaction mixture was refluxed for four hours, cooled to 250° C. and filtered to collect the tetramethyl titanate. The tetramethyl titanate was washed twice with 150 cc of methanol and once with 150 cc of pentane. The final product was vacuum dried at room temperature at 1 mm Hg. The yield of final product was 88% based on titanium tetrachloride. Titanium analysis showed 27.6% titanium (27.86% theory).

EXAMPLE 2

Similar to Example 1 except trioctylamine was used as an HCl acceptor. The final yield was 78%. Titanium analysis was 27.8% (27.9% theory).

EXAMPLE 3

Similar to Example 1 except tripropylamine was used as an HCl acceptor. The final yield was 77%.

EXAMPLE 4

Table I summarizes the different amines used and the toluene/alcohol ratios employed.

TABLE I

| ml Toluene/ ml $CH_3OH$ | Amine | Total Liquid Volume (Toluene, $CH_3OH$, Amine) | Yield |
| --- | --- | --- | --- |
| 225/90 | Trioctylamine | 395 cc | 78% |
| 200/90 | Tributylamine | 365 cc | 78% |

TABLE I-continued

| ml Toluene/ ml CH$_3$OH | Amine | Total Liquid Volume (Toluene, CH$_3$OH, Amine) | Yield |
| --- | --- | --- | --- |
| 90/170 | Tripropylamine | 217 cc | 77% |
| 90/120 | Triethylamine | 250 cc | 60% |
| 140/60 | Tributylamine | 275 cc | 88% |
| 120/50 | Tributylamine | 245 cc | 88% |

EXAMPLE 5

This example illustrates that the two step process can be adapted so as to carry out step I using toluene, thereby eliminating the need for toluene in the second step.

To a 500 milliliter, 3-necked flask equipped with a condenser and nitrogen inlet tube were added, under nitrogen, 35 grams (0.184 mole) of titanium tetrachloride and 200 cc of toluene. To this solution was added 20 cc of methanol. Nitrogen was passed through the solution to remove the hydrogen chloride formed. The mixture was then transferred to a flask and the solvent was removed on a rotary evaporator at 50° C. at 15 mm Hg. The solid which remained (33.8 grams) was dissolved in 190 cc of methanol in a 500 milliliter, 3-necked flask equipped with a condenser, dropping funnel and mechanical stirrer. 41 grams of (0.4 mole) of triethylamine was added dropwise over a 30 minute period. Upon addition of the amine, the tetramethyl titanate immediately precipitated out. The reaction mixture was refluxed for 3 hours and then filtered using an airless filtering funnel. The product was washed twice with 100 cc of methanol and once with 150 cc of pentane. The material was then vacuum dried for 2 hours at 1 mm Hg. The yield of tetramethyl titanate was 26.6 grams (84% of theory).

EXAMPLE 6

This example illustrates that tetramethyl titanate can be made in a one step process.

To a 500 milliliter 3-necked flask equipped with a stirrer, addition funnel and condenser were added 200 cc of dry methanol and 35 grams (0.184 mole) of titanium tetrachloride. The reaction mixture was blanketed under nitrogen, heated to reflux and cooled to room temperature. At 250° C., 80 grams (0.8 mole) of triethylamine was added and the mixture was heated at reflux temperature for 4 hours. The resulting product was filtered through an airless filtering funnel, washed once with 200 cc of heptane and then vacuum dried for 3 hours at 25° C. at 1 mm Hg. The final yield was 60% based on titanium tetrachloride.

EXAMPLE 7

By carrying out Examples 1 to 6 under the reaction conditions described, and using as a hydrogen halide acceptor a tertiary C$_8$-C$_{16}$ amine, such as ALAMINE ® 336 amine, a final product is obtained.

Additional features of the preferred and most preferred embodiments of the present invention are found in the claims hereinafter.

What is claimed is:

1. A process for the production of metal alkoxides selected from the group consisting of alkoxides of strontium, barium, gallium, indium, boron, yttrium, titanium, zirconium, and hafnium, said alkoxides being insoluble in organic solvents, which process comprises:
    (a) reacting a halide of an at least divalent metal with an alcohol to form an intermediate compound, said intermediate compound being a halo alkoxy metal compound; and
    (b) reacting the intermediate compound of (a) with an alcohol, said alcohol forming part of an organic solvent system, in the presence of a hydrogen halide acceptor, said hydrogen halide acceptor forming a hydrogen halide compound soluble in the organic solvent system.

2. The process of claim 1 wherein said metal alkoxide produced is the metal methoxide.

3. The process of claim 1 wherein said metal alkoxide is tetramethyl titanate.

4. The process of claim 5 wherein said metal alkoxide is selected from the group consisting of methoxides of strontium, barium, gallium, indium, boron, yttrium, titanium, zirconium and hafnium.

5. The process of claim 1 wherein said halide of a metal is titanium tetrachloride.

6. The process of claim 1 wherein said intermediate compound is dichloro, dimethyl titanate.

7. A process for the production of metal alkoxides selected from the group consisting of alkoxides of strontium, barium, gallium, indium, boron, yttrium, titanium, zirconium, and hafnium, said alkoxides being insoluble in organic solvents which process comprises:
    (a) reacting a halide of an at least divalent metal with an alcohol in the presence of a solvent which is substantially inert towards the hydrogen halide formed to produce an intermediate, said intermediate being a halo alkoxy metal compound;
    (b) isolating the intermediate of (a) and stripping said solvent from said intermediate to produce a solid product; and
    (c) dissolving said solid product in the alcohol of (a) in the presence of a hydrogen halide acceptor, said hydrogen halide acceptor forming a hydrogen halide compound soluble in said alcohol.

8. The process of claim 7 wherein said metal alkoxide is tetramethyl titanate.

9. The process of claim 7 wherein said metal alkoxide is selected from the group consisting of methoxides of strontium, barium, gallium, indium, boron, yttrium, titanium, zirconium and hafnium.

10. The process of claim 7 wherein said halide of a metal is titanium tetrachloride.

11. The process of claim 7 wherein said intermediate compound is dichloro, dimethyl titanate.

12. A one-step process for the production of a metal alkoxide selected from the group consisting of alkoxides of strontium, barium, gallium, indium, boron, yttrium, titanium, zirconium and hafnium, said alkoxide being insoluble in organic solvent, said alkoxide represented by the formula:

$$M(OR)_n$$

wherein M is at least a divalent metal, R is alkyl, and n is as defined below, which process comprises dissolving a halide of an at least divalent metal in an alcohol, said metal halide represented by the formula:

$$MX_n$$

wherein M is as previously defined, X is a halogen, and n is an integer from 2 to 4; said alcohol also being reactive with said metal halide, said process also being conducted in the presence of an excess amount of a hydrogen halide acceptor, said amount of acceptor being over the amount of halide atoms on the metal halide, and said hydrogen halide acceptor forming a hydrogen halide compound soluble in said alcohol.

13. The process of claim 12 wherein said tetramethyl metal alkoxide is tetramethyl titanate.

14. The process of claim 12 wherein said metal alkoxide is selected from the group consisting of methoxides of strontium, barium, gallium, indium, boron, yttrium, titanium, zirconium and hafnium.

15. The process of claim 12 wherein said metal halide is titanium tetrachloride.

16. The process of claim 12 wherein the metal of the metal alkoxide is selected from strontium, barium, titanium, zirconium, and hafnium.

17. The process of claim 16 wherein the metal is selected from titanium, zirconium, and hafnium.

* * * * *

UNITED STATES PATENT AND TRADEMARK OFFICE
CERTIFICATE OF CORRECTION

PATENT NO. : 4,681,959

DATED : July 21, 1987

INVENTOR(S) : Richard J. Ayen et al.

It is certified that error appears in the above-identified patent and that said Letters Patent are hereby corrected as shown below:

Col. 2, line 31, "present" should be "presence";

Col. 5, line 32, "tri" should read "tri-"; and

Col. 8, line 15, "claim 5" in line 1 of claim 4 should read "claim 1".

Signed and Sealed this

Twelfth Day of January, 1988

Attest:

DONALD J. QUIGG

*Attesting Officer*  *Commissioner of Patents and Trademarks*